US007291570B1

(12) United States Patent
Green et al.

(10) Patent No.: US 7,291,570 B1
(45) **Date of Patent: *Nov. 6, 2007**

(54) YARNS AND FABRICS HAVING A WASH-DURABLE NON-ELECTRICALLY CONDUCTIVE TOPICALLY APPLIED METAL-BASED FINISH

(75) Inventors: David E. Green, Simpsonville, SC (US); Dirk L. Van Hyning, Spartanburg, SC (US); Leland G. Close, Jr., Spartanburg, SC (US); Shulong Li, Spartanburg, SC (US); Robert J. Goulet, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/586,381

(22) Filed: Jun. 2, 2000

(51) Int. Cl.
*B32B 5/02* (2006.01)
*B32B 27/04* (2006.01)
*C11D 3/00* (2006.01)

(52) U.S. Cl. ...................... 442/123; 428/340; 428/341; 428/342; 252/8.82; 8/115.51

(58) Field of Classification Search ................ 442/123; 428/340, 341, 342; 252/8.82; 8/115.51
See application file for complete search history.

(56) References Cited

U.S. PATENT DOCUMENTS 4,524,170 A 6/1985 Berczi et al.
5,265,770 A 11/1993 Matkovich et al. ......... 222/189
5,427,844 A 6/1995 Murai et al. ................ 428/245
5,432,000 A * 7/1995 Young, Sr. et al. ......... 428/372
5,849,311 A * 12/1998 Sawan et al. ............... 424/406
5,981,063 A * 11/1999 Yokozeki et al. ........... 428/365
6,004,889 A 12/1999 Ichikawa
6,149,927 A * 11/2000 Ghosh ........................ 424/405
6,584,668 B2 * 7/2003 Green et al. ............... 29/527.2
6,640,371 B2 * 11/2003 Green et al. ................... 8/155
6,641,829 B1 * 11/2003 Green et al. ................ 424/405
6,821,936 B2 * 11/2004 Green et al. ................ 510/319
6,946,433 B2 * 9/2005 Green et al. ................ 510/319

FOREIGN PATENT DOCUMENTS

GB 2185998 * 8/1987
JP H11-124729 5/1999

* cited by examiner

*Primary Examiner*—N. Bhat
(74) *Attorney, Agent, or Firm*—Terry T. Moyer; Brenda D. Wentz

(57) ABSTRACT

Durable non-electrically conductive metal treatments (such as coatings or finishes) for yarns and textile fabrics. Such treatments preferably comprise silver and/or silver ions; however, other metals, such as zinc, iron, copper, nickel, cobalt, aluminum, gold, manganese, magnesium, and the like, may also be present or alternatively utilized. Such a treatment provides, as one example, an antimicrobial fiber and/or textile fabric which remains on the surface and does not permit electrical conductivity over the surface. The treatment is extremely durable on such substrates; after a substantial number of standard launderings and dryings, the treatment does not wear away in any appreciable amount and thus the substrate retains its antimicrobial activity (or other property). The method of adherence to the target yarn and/or fabric may be performed any number of ways, most preferably through the utilization of a binder system or through a transfer method from a donor fabric to a target textile fabric in the presence of moisture and upon exposure to heat. The particular methods of adherence, as well as the treated textile fabrics and individual fibers are also encompassed within this invention.

12 Claims, No Drawings

YARNS AND FABRICS HAVING A WASH-DURABLE NON-ELECTRICALLY CONDUCTIVE TOPICALLY APPLIED METAL-BASED FINISH

FIELD OF THE INVENTION

This invention relates to improvements in durable non-conductive metal-based treatments (such as coatings or finishes) for yarns and textile fabrics. Such treatments preferably comprise silver and/or silver ions; however, other metals, such as zinc, iron, copper, nickel, cobalt, aluminum, gold, manganese, magnesium, and the like, may also be present or alternatively utilized. Such a treatment provides, as one example, an antimicrobial fiber and/or textile fabric which remains on the surface and does not permit electrical conductivity over the surface. The treatment is extremely durable on such substrates; after a substantial number of standard launderings and dryings, the treatment does not wear away in any appreciable amount and thus the substrate retains its antimicrobial activity (or other property). The method of adherence to the target yarn and/or fabric may be performed any number of ways, most preferably through the utilization of a binder system or through a transfer method from a donor fabric to a target textile fabric in the presence of moisture and upon exposure to heat. The particular methods of adherence, as well as the treated textile fabrics and individual fibers are also encompassed within this invention.

DISCUSSION OF THE PRIOR ART

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; *Salmonella* contamination causing sicknesses from undercooked and unwashed poultry food products; and illnesses and skin infections attributed to *Staphylococcus aureus, Klebsiella pneumoniae*, yeast, and other unicellular organisms. With such an increased consumer interest in this area, manufacturers have begun introducing antimicrobial agents within various household products and articles. For instance, certain brands of polypropylene cutting boards, liquid soaps, etc., all contain antimicrobial compounds. The most popular antimicrobial for such articles is triclosan. Although the incorporation of such a compound within liquid or polymeric media has been relatively simple, other substrates, including the surfaces of textiles and fibers, have proven less accessible. There is a long-felt need to provide effective, durable, and long-lasting antimicrobial characteristics for textile surfaces, in particular on apparel fabrics, and on film surfaces. Such proposed applications have been extremely difficult to accomplish with triclosan, particularly when wash durability is a necessity (triclosan easily washes off any such surfaces). Furthermore, although triclosan has proven effective as an antimicrobial compound, the presence of chlorines and chlorides within such a compound causes skin irritation which makes the utilization of such with fibers, films, and textile fabrics for apparel uses highly undesirable. Furthermore, there are commercially available textile products comprising acrylic and/or acetate fibers co-extruded with triclosan (for example Celanese markets such acetate fabrics under the name Microsafe™ and Acordis markets such acrylic fibers under the tradename Amicor™). However, such an application is limited to those types of fibers; it does not work specifically for and within polyester, polyamide, cotton, spandex, etc., fabrics. Furthermore, this co-extrusion procedure is very expensive.

Silver-containing inorganic microbiocides have recently been developed and utilized as antimicrobial agents on and within a plethora of different substrates and surfaces. In particular, such microbiocides have been adapted for incorporation within melt spun synthetic fibers, as taught within Japanese unexamined Patent Application No. H11-124729, in order to provide certain fabrics which selectively and inherently exhibit antimicrobial characteristics. Furthermore, attempts have been made to apply such specific microbiocides on the surfaces of fabrics and yams with little success from a durability standpoint. A topical treatment with such compounds has never been successfully applied as a durable finish or coating on a fabric or yam substrate. Although such silver-based agents provide excellent, durable, antimicrobial properties, to date such is the sole manner available within the prior art of providing a long-lasting, wash-resistant, silver-based antimicrobial textile. However, such melt spun fibers are expensive to make due to the large amount of silver-based compound required to provide sufficient antimicrobial activity in relation to the migratory characteristics of such a compound within the fiber itself to its surface. A topical coating is also desirable for textile and film applications, particularly after finishing of the target fabric or film. Such a topical procedure permits treatment of a fabric's individual fibers prior to or after weaving, knitting, and the like, in order to provide greater versatility to the target yam without altering its physical characteristics. Such a coating, however, must prove to be wash durable, particularly for apparel fabrics, in order to be functionally acceptable. Furthermore, in order to avoid certain problems, it is highly desirable for such a metallized treatment to be electrically non-conductive on the target fabric, yarn, and/or film surface. With the presence of metals and metal ions, such a wash durable, non-electrically conductive coating has not been available in the past. Such an improvement would thus provide an important advancement within the textile, yam, and film art. Although antimicrobial activity is one desired characteristic of the inventive metal-treated fabric, yarn, or film, this is not a required property of the inventive article. Odor-reduction, heat retention, distinct colorations, reduced discolorations, improved yam and/or fabric strength, resistance to sharp edges, etc., are all either individual or aggregate properties which may be accorded the user of such an inventive treated yarn, fabric, or film.

DESCRIPTION OF THE INVENTION

It is thus an object of the invention to provide a simple manner of effectively treating a yarn, textile, or film with a wash-durable antimicrobial metal or metal-ion containing treatment. A further object of the invention is to provide a treatment for textiles or films which is wash-durable and continuously reduces and/or removes malodors from the target surface through the utilization of metals or metal-ions. Another object of the invention is to provide an aesthetically pleasing metal- or metal-ion-treated textile or film which is non-electrically conductive, wash durable, non-yellowing, non-irritating to skin, and which provides either or both antimicrobial or odor-reducing properties.

Accordingly, this invention encompasses a treated substrate comprising a non-electrically conductive treatment comprising metal-containing compounds selected from the group consisting of metal particle-containing compounds, metal ion-containing compounds, and any combinations thereof, and a substrate selected from the group consisting of a yam, a fabric comprised of individual yarns, and a film; wherein said compound or compounds is present on at least a portion of the surface of said substrate; and wherein at least about 30%, of the originally adhered metal-containing treatment remains on said treated portion of said substrate surface after at least 10 washes, said washes being performed in accordance with the wash procedure as part of AATCC Test Method 130-1981. Still more preferably at least 50% of the metal-containing compounds remain after 10 washes, more preferably 60% after 10 washes, and most preferably at least 75% after the same number of washes. Furthermore, it is also highly preferred that at least 30% of the finish is retained after 15 washes, 20 washes, and most preferably about 30 washes. Also, and alternatively, this invention encompasses a treated substrate comprising a non-electrically conductive treatment comprising metal-containing compounds selected from the group consisting of metal particle-containing compounds, metal ion-containing compounds, and any combinations thereof, and a substrate selected from the group consisting of a yarn, a fabric comprised of individual yams, and a fihn; wherein said compound or compounds is adhered to at least a portion of the surface of said substrate; and wherein said treated substrate exhibits a log kill rate for *Staphylococcus aureus* of at least 1.5, preferably above 2.0, more preferably above 3.0, and a log kill rate for *Klebsiella pneumoniae* of at least 1.5, preferably above 2.0, and more preferably above 3.0, both as tested in accordance with AATCC Test Method 100-1993 for 24 hour exposure, after at least 10 washes, said washes performed in accordance with the wash procedure as part of AATCC Test Method 130-1981. Such an invention also encompasses the different methods of producing such a treated substrate. The wash durability test noted above is standard and, as will be well appreciated by one of ordinary skill in this art, is not intended to be a required or limitation within this invention. Such a test method merely provides a standard which, upon 10 washes in accordance with such, the inventive treated substrate will not lose an appreciable amount of its electrically non-conductive metal finish.

The amount retained may be measured in any standard manner, such as, for example, inductively coupled plasma (ICP), X-ray fluorescence (XRF), or atomic absorption (AA) spectroscopic analysis. Or, again, in the alternative, the durability of certain finishes may be determined (i.e., the retention of finish on the surface) in relation to antimicrobial performance. Thus, with an antimicrobially effective finish, the exhibition of log kill rates for *Klebsiella pneumoniae* or *Staphylococcus aureus* after 24 hours exposure in accordance with AATCC Test Method 100-1993 of at least 1.5, and higher, as noted above, for both after 10 washes in accordance with AATCC Test Method 130-1981. Preferably, these log kill rates are above 3.2, more preferably 3.5, and most preferably at least 4.0. Again, such log kill rates after the minimum number of washes symbolizes the desired durability level noted above.

Nowhere within the prior art has such a specific treated substrate or method of making thereof been disclosed, utilized, or fairly suggested. The closest art is a product marketed under the tradename X-STATIC® which is a fabric article electrolessly plated with a silver coating. Such a fabric is highly electrically conductive and is utilized for static charge dissipation. Also, the coating alternatively exists as a removable silver powder finish on a variety of surfaces. The aforementioned Japanese patent publication to Kuraray is limited to fibers within which a silver-based compound has been incorporated through melt spun fiber techniques. Nowhere has such a wash-durable topical treatment as now claimed been mentioned or alluded to.

Any yarn, fabric, or film may be utilized as the substrate within this application. Thus, natural (cotton, wool, and the like) or synthetic fibers (polyesters, polyamides, polyolefins, and the like) may constitute the target substrate, either by itself or in any combinations or mixtures of synthetics, naturals, or blends or both types. As for the synthetic types, for instance, and without intending any limitations therein, polyolefins, such as polyethylene, polypropylene, and polybutylene, halogenated polymers, such as polyvinyl chloride, polyesters, such as polyethylene terephthalate, polyester/polyethers, polyamides, such as nylon 6 and nylon 6,6, polyurethanes, as well as homopolymers, copolymers, or terpolymers in any combination of such monomers, and the like, may be utilized within this invention. Nylon-6, nylon-6,6, polypropylene, and polyethylene terephthalate (a polyester) are particularly preferred. Additionally, the target fabric may be coated with any number of different films, including those listed in greater detail below. Furthermore, the substrate may be dyed or colored to provide other aesthetic features for the end user with any type of colorant, such as, for example, poly(oxyalkylenated) colorants, as well as pigments, dyes, tints, and the like. Other additives may also be present on and/or within the target fabric or yarn, including antistatic agents, brightening compounds, nucleating agents, antioxidants, UV stabilizers, fillers, permanent press finishes, softeners, lubricants, curing accelerators, and the like. Particularly desired as optional and supplemental finishes to the inventive fabrics are soil release agents which improve the wettability and washability of the fabric. Preferred soil release agents include those which provide hydrophilicity to the surface of polyester. With such a modified surface, again, the fabric imparts improved comfort to a wearer by wicking moisture. The preferred soil release agents contemplated within this invention may be found in U.S. Pat. Nos. 3,377,249; 3,540,835; 3,563,795; 3,574,620; 3,598,641; 3,620,826; 3,632,420; 3,649,165; 3,650,801; 3,652,212; 3,660,010; 3,676,052; 3,690,942; 3,897,206; 3,981,807; 3,625,754; 4,014,857; 4,073,993; 4,090,844; 4,131,550; 4,164,392; 4,168,954; 4,207,071; 4,290,765; 4,068,035; 4,427,557; and 4,937,277. These patents are accordingly incorporated herein by reference. Additionally, other potential additives and/or finishes may include water repellent fluorocarbons and their derivatives, silicones, waxes, and other similar water-proofing materials.

The particular treatment must comprise at least one type of metal-incorporating compound (namely metal particles), metal-ion containing particles, or mixtures thereof. The term metal is intended to include any such historically understood member of the periodic chart (including transition metals, such as, without limitation, silver, zinc, copper, nickel, iron, magnesium, manganese, vanadium, gold, cobalt, platinum, and the like, as well as other types including, without limitation, aluminum, tin, calcium, magnesium, antimony, bismuth, and the like). More preferably, the metals utilized within this invention are generally those known as the transition metals. Of the transition metals, the more preferred metals are silver, zinc, gold, copper, nickel, manganese, and iron. Most preferred are silver and zinc. Such metals provide the best overall desired characteristics, such as, preferably, antimicrobial and/or odor reducing characteristics, certain colorations, good lightfastness, and, most importantly, wash durability on the target substrate.

The term metal particle is intended to encompass any compound within which the metal is present in its pure non-ionic state (thus silver particles are present, as one example). The term metal-ion containing encompasses compounds within which the ionic species of metals are present (such as metal oxides, including, as mere examples, zinc oxide for $Zn^{2+}$, silver oxide for $Ag^{+}$, and iron oxide for $Fe^{2+}$ or $Fe^{3+}$, or, as alternatives, ion-exchange resins, zeolites, or, possibly substituted glass compounds, which release the particular metal ion bonded thereto upon the presence of other anionic species). The preferred metal particle compound is produced through a reduction procedure and may be any of silver, nickel, copper, zinc, and iron. With a reducing agent, the salts utilized for this purpose are thus preferably silver (I) nitrate, nickel (II) perchlorate, copper (II) acetate, and iron (II) sulfate. The preferred metal-ion containing compound for this invention is an antimicrobial silver zirconium phosphate available from Milliken & Company, under the tradename ALPHASAN®, although any silver-containing antimicrobial compound, including, for instance, and as merely some examples, a silver-substituted zeolite available from Sinanen under the tradename ZEOMIC® AJ, or a silver-substituted glass available from Ishizuka Glass under the tradename IONPURE®, may be utilized either in addition to or as a substitute for the preferred species. Also preferred as such a compound is zinc oxide, zinc ricinoleate, zinc chloride, and zinc sulfate. Other metals, as noted above, may also be utilized; however, from a performance standpoint, silver and zinc, are most preferred. Generally, such a metal compound is added in an amount of from about 0.01 to 40% by total weight of the particular treatment composition; more preferably from about 0.05 to about 30%; and most preferably from about 0.1 to about 3 0%, all dependent upon the selected method of application. The metal compound is then added to the target substrate in a) amounts of between 0.01 and 1.0 ounces per square yard, or, alternatively, b) from about 0.01 to about 5% owf, depending on the selected application and method for measuring. Such proportions provide the best antimicrobial and/or odor-reducing performance in relation to wash durability, electrical non-conductivity, and overall cost. Preferably this metal compound add-on weight is a) about 0.1, or b) about 1.0% owf. The treatment itself, including any necessary binders, adherents, thickeners, and the like, is added to the substrate in an amount of a) about 0.01 to about 4.0 ounces per square yard, or b) from about 0.01 to about 10% owf.

Furthermore, the inventive substrates necessarily do not exhibit any appreciable electrical conductivity (due to the low amounts of metal present and thus the nonexistence of any percolation over or through the target substrate) as measured by attaching a two-inch by two-inch fabric specimen to two electrodes and applying a voltage gradient of about 100 volts per inch through the fabric (i.e., in accordance with AATCC Test Method 76-1978). The measured resistance in ohms per square inch should exceed about 10,000, preferably 1,000,000, and most preferably 1×110 in order to provide a substantially non-electrically conductive fabric.

The selected substrate may be any of an individual yarn, a fabric comprising individual fibers or yarns (though not necessarily previously coated yarns), or a film (either standing alone or as laminated to a fabric, as examples). The individual fibers or yarns may be of any typical source for utilization within fabrics, including natural fibers (cotton, wool, ramie, hemp, linen, and the like), synthetic fibers (polyolefins, polyesters, polyamides, polyaramids, acetates, rayon, acylics, and the like), and inorganic fibers (fiberglass, boron fibers, and the like). The target yarn may be of any denier, may be of multi- or mono-filament, may be false-twisted or twisted, or may incorproate multiple denier fibers or filaments into one single yarn through twisting, melting, and the like. The target fabrics may be produced of the same types of yarns discussed above, including any blends thereof. Such fabrics may be of any standard construction, including knit, woven, or non-woven forms. The films may be produced from any thermoplastic or thermoset polymer, including, but not limited to, polyolefins (polypropylene, polyethylene, polybutylene), polyvinyl chloride, polyvinylidene chloride, polyvinyl acetate, and the like, polyesters (polyethylene terephthalate, isophthalates, and the like) polyethers, acetates, acrylics, and polyamides, as well as any copolymer films of any of the above. Such films may be extruded, blown, rolled, and the like, and may be produced in situ on the surface of a target fabric or produced separately and subsequently adhered or laminated on a target surface. Also, such films may be produced, treated, and utilized separately from any other substrates.

The yarns are preferably incorporated within specific fabrics, although any other well known utilization of such yarns may be undertaken with the inventive articles (such as tufting for carpets). The inventive fabrics may also be utilized in any suitable application, including, without limitation, apparel, upholstery, bedding, wiping cloths, towels, gloves, rugs, floor mats, drapery, napery, bar runners, textile bags, awnings, vehicle covers, boat covers, tents, and the like. The inventive films may be present on fabrics, or utilized for packaging, as coatings for other types of substrates, and the like.

Yarn and fabric substrates are preferably treated with a metal particle or metal-ion containing finish. Films are preferably treated with metal-ion containing formulations on the surface of film-coated fabrics.

Metal Particle Treatments

The preferred metal particle composition will generally comprise four components: water, a metal salt, a reducing agent, and a polymeric binder. As noted above, the metal is produced through the reduction of the metal ion upon dissolution of the metal salt in solution. This specific process actually blends two different technologies, specifically the formation of colloidal particles by chemical reduction and steric stabilization of such particles by surfactant or polymer and the modification of a fiber (or textile) surface through the utilization of a polymeric binder. In the instance, the steric stabilizer and the fiber (or textile) binder are the same polymeric compound.

Such a metal particle dispersion is generally produced as follows: A solution of the polymeric binder and water is produced having a polymer concentration between 0.1% and 20% (w/w). The solution is then divided between two containers, one containing a dissolved metal salt (i.e. a metal salt MA dissociates completely to $M^{+}$ and $A^{-}$) and in the other, a dissolved reducing agent. When the two solutions are thoroughly mixed, they are then combined very quickly. When combined, the reducing agent transfers an electron to the metal cation and reduces it to its neutral form ($M_n^{+}+e^{-} \rightarrow M_n^{0}$). The metal atoms quickly agglomerate to form larger (1-1000 nm) particles. The steric stabilizer acts by adsorbing to the surface of the growing particles and thereby prevents catastrophic flocculation of the particles into macroscopic (~mm in diameter) aggregates by limiting the distance of closest approach.

It is important to note that the selection of the particular polymeric binder is crucial to the success in attaining the desired durability and effectiveness of the specific coating as this binder component must meet a number of important criteria. First, since high salt concentrations are necessary to generate large numbers of metal particles, and such salts generally cause many polymeric binder dispersions to flocculate out of solution, the particular binder must not react in such a manner in order to effectively stabilize the particles that are produced (as noted above). Secondly, the binder must not act like typical textile binders (which do not stabilize the particles and thus allow the nucleated particles to flocculate rapidly into macroscopic assemblies) which would render the resultant solution unusable in this application. Thirdly, it is important that the polymeric stabilizer, once processed, be able to withstand home washing under a wide range of conditions and maintain the silver concentration on the textile. Thus, it must not be readily soluble in water, must not be susceptible to attack by standard and/or industrial detergents, solvents, and/or bleaches, and must not melt upon exposure to drying temperatures. The utilization of such a specific binder to provide a metal coating to fibers and/or fabrics is thus drastically different from other previous practices in this area and permits a topical application of a such a coating either before or after the particular substrate has been finished. In order to provide the requisite wash durability, this binder must pass these stringent criteria. No teaching or fair suggestion exists within the prior art of such requirements.

As noted previously, the preferred metal salts for this procedure are silver (I) nitrate, nickel (II) perchlorate, copper (II) acetate, and iron (II) sulfate. The concentrations of these salts within the immersion bath can be increased to 2% before the kinetics of reduction and aggregation overwhelm the kinetics of polymer adsorption and mixing and cause significant aggregation/clumping of the metal. The preferred metal salt is silver (I) nitrate and is present in a concentration of from about 0.01% to about 10%, more preferably from about 0.1% to about 5.0%, and most preferably about 1.0% within the immersion bath.

The preferred reducing agents are sodium borohydride ($NaBH_4$), sodium hydrosulfite, and trisodium citrate ($Na_3C_6H_5O_7$), although any standard reducing agent associated with the above-listed metal salts may be utilized. The former is a stronger reducing agent that reacts with the metal completely within seconds of mixing. An undesirable byproduct of this reaction is hydrogen gas that causes significant foaming when mixed. The latter two do not have this effect, but are milder reducing agents and require heating to near boiling to cause the reaction to proceed.

The polymeric binder may be selected from certain resins and thermoplastics, such as melamine resins and polyvinyl chloride-containing polymers. Of particular interest, and thus the preferred polymeric binders for this process are melamine-formaldehyde resins (such as a resin available from BFGoodrich under the tradename Aerotex®), polyvinyl chloride/vinyl copolymers (such as a copolymer also available from BFGoodrich under the tradename Vycar® 460×49), and PVC/acrylic resins available from BFGoodrich. It has been found that upon exposure to an ammonium sulfate catalyst and curing at 350° C. for 2 minutes, the melamine provides durable finish on either a fiber or a fabric of at least 30 washes. The copolymer requires no catalyst and performs similarly to the melamine in wash durability when cured for the same time and at the same temperature. (Table 1 lists the ICP reading for silver as a function of home washes using Aerotex® M3 and BFG Vycar® in a pad.)

The solution described above can be applied to fabric or yarn in a number of ways. Included in this list, which is by no means exhaustive, are pad coating, screen coating, spraying, and kiss-coating (particularly for yarn applications). The preferred coating and method are discussed in greater depth below.

Metal-Ion Containing Coatings

The preferred procedures utilizing metal-ion containing compounds include any of the following, depending on the desired characteristics of the final product. One alternative utilizes the silver-ion compound noted above, such as either ALPHASAN®, ZEOMIC®, or IONPURE® as preferred compounds (although any similar types of compounds which provide silver ions may also be utilized), exhausted on the target fabric or film surface and then overcoated with a binder resin. Alternatively, the metal-ion containing compound may be admixed with a binder within a dye bath, into which the target fabric or fiber is then immersed at elevated temperatures (i.e., above about 50° C.).

Such a procedure was developed through an initial attempt at understanding the ability of such metal-ion containing compounds to attach to a fabric surface. Thus, a sample of ALPHASAN® was first exhausted from a dye bath on to a target polyester fabric surface. The treated fabric exhibited excellent log kill rate characteristics; however, upon washing in a standard laundry method (AATCC Test Method 130-1981, for instance), the antimicrobial activity was drastically reduced. Such promising initial results led to the inventive wash-durable antimicrobial treatment wherein the desired metal-ion containing compound would be admixed or overcoated with a binder resin on the target fabric surface. The binder resin should exhibit little or no water solubility (substantially water-insoluble), and must readily adhere to either the fabric surface or to the metal-ion containing compound itself. Such a binder resin can thus be selected from the group consisting of nonionic permanent press binders (i.e., cross-linked adhesion promotion compounds, including, without limitation, cross-linked imidazolidinones, available from Sequa under the tradename Permafresh®) or slightly anionic binders (including, without limitation, acrylics, such as Rhoplex® TR3082 from Rohm & Haas). Other nonionics and slightly anionics may be utilized as long as they provide the desired adhesion characteristics. Such potential compounds include melamine formaldehyde, melamine urea, ethoxylated polyesters, such as Lubril QCX™ available from Rhodia, and the like. The initial exhaustion of ALPHASAN® is thus preferably followed by a thin coating of binder resin to provide the desired wash durability characteristics for the metal-based particle treatment. The antimicrobial characteristics of the treated fabric remained very effective for the fabric even after as many as ten standard laundering procedures. Also possible, though less effective as compared to the aforementioned binder resin overcoat, but still an acceptable method of providing a wash-durable antimicrobial metal-treated fabric surface, is the application of a metal-ion containing compound/binder resin from a dye bath mixture. The exhaustion of such a combination is less efficacious from an antimicrobial activity standpoint than the overcoat procedure, but, again, still provides a wash-durable treatment with acceptable antimicrobial benefits. In actuality, this mixture of compound/resin may be applied through spraying, dipping, padding, and the like.

Another preferred alternative concerns the treating of individual fibers. Such an alternative has proven very effective, most particularly in a package dyeing method. In such a procedure, a dye bath comprising the desired metal-ion containing compounds and binder agents is pumped through a tightly wound spool of yarn (or fiber). This is generally a rather difficult process to perform effectively since the particle sizes of the constituent dye bath solids might interfere with the requisite pump pressure to force the dye bath liquor through the entire "package" of yarn. Furthermore, such a dyeing method must produce a uniform treatment of all the portions of the target yarn throughout the "package"; particle size and thoroughness of mixing are thus of vital importance to impart of even treatment over the entire yarn. Surprisingly, this procedure works very well for imparting a wash-durable metal treatment on the yarn surface. Upon treatment of target yarns, such yarns can then be woven, knit, or incorporated within a non-woven fabric structure to form a textile. The textile exhibits similar colorations, log kill rates, and the like, at discrete locations of the textile. Without intending to be bound to any specific theory, it is believed that the binding agent appears to affix itself over the metal-ion containing compounds adhered to the yarn surface, or that the binding agent adheres to the yarn surface, to which the metal-ion containing compound then affixes itself (and to which binding agent may also affix). As such, and again, very surprisingly, the desired metal-ion containing compounds were small enough to be forced through the yarn "package" in order to treat the entire target yarn.

In such an alternative method, the high pressure procedure necessary for providing the antimicrobial solid application on the surface of the target yarns must be sufficient to permit penetration of the solid compounds into the actual yarn structure. A high temperature may be desired to permit "opening" of the fiber structure to facilitate such solids introduction within a solid yarn. In general, the high pressure conditions must be from about 0.1 and 100 pounds per square inch with an exposure time of from about 5 seconds to about 5 hours at a temperature in the range from about 25° to about 325° C. Such conditions are most readily provided within a jet dye, closed vessel system, and appears to work most readily for package dyed yarns. The type of fiber is consequential only to the extent that certain temperatures permit easier penetration within certain fibers. Thus, natural fibers (such as cotton) require relatively low temperatures to "open" of the cellulosic structure; nylon requires a much higher temperature (to exceed its glass transition temperature, typically) to provide the most effective antimicrobial characteristics. For the most part, the high pressure actually appears to force the solid particles into the yarns; surprisingly, such solid-solid interaction works to retain a substantial amount of the solid antimicrobial, even after washing. Preferably, however, a binder agent is added to aid in solid particle retention since such solid particles will most likely exhibit a desire to become detached from the yarn over time.

Another alternative utilizes a metal oxide treatment on a fabric or film surface, such as, preferably, zinc oxide, coated with a hydrophobic binding agent mixed with a synergistic amount of a polymeric hydrophilic material, applied to a fabric or film surface, primarily to provide a wash-durable odor-reducing finish on the target fabric. Generally, the presence of such a wash-durable hydrophobic binding agent is possible only on a hydrophobic fabric surface. However, hydrophobic fabric does not wick moisture and thus is very uncomfortable to wear (if utilized as apparel fabric) as compared to a hydrophilic moisture-wicking fabric. Also, such a hydrophobic binding agent overcoat for the metal oxide odor-reducing material would detrimentally mask the metal oxide surface and retard the odor neutralizing action of the effective compound, particularly when present on and/or in a wet fabric. However, in order to provide a wash-durable metal oxide odor-reducing finish to a textile or fabric, seemingly there is a need to provide a complete hydrophobic binding agent over the metal oxide. When such a "required" excess of hydrophobic agent binder is present, again, the metal oxide (i.e., zinc oxide) would most likely be encapsulated and thus will not contact the targeted odor-producing compounds. A reduction in such hydrophobic binding agent results in a lack of sufficient adhesion between the metal oxide particles and the target fabric to provide a wash-durable and wear-durable finish. It was found, surprisingly, that the necessary comfort (due to wicking of moisture) and simultaneous retention of sufficient adhesion are provided through the addition of a hydrophilic agent to the zinc oxide/binding agent formulation. With such an addition, a durable, moisture-wicking, and odor-reducing textile finish/coating is provided. Of great and surprising interest is the apparent synergistic interaction between the zinc oxide, binding agent and hydrophilic agent. The hydrophilic agent not only provides moisture-wicking comfort to the target fabric, but also facilitates the interaction of odor compounds in human perspiration with the preferred zinc oxide to allow efficient odor neutralization. In general the weight ratio of zinc oxide to resin binder is in the range of 100:1 to 1:100 to be effective. The ratio between 1:2 and 2:1 is preferred. One suitable wetting agent for this application may possess both hydrophilic and hydrophobic moieties within its structure. In such an instance, the specific hydrophilic moiety must be present in an amount sufficient to permit any moisture spread on the treated fabric surface. The finish also requires sufficient amounts of a hydrophobic moiety within its structure to make it water soluble. As a result, the finish will not be easily washed off in repeated washing cycles. Examples of such preferred wetting agents are sulfonated polyesters, ethylene oxide-propylene oxide copolymers, and ethoxylated polyesters. The preferred metal oxide is zinc oxide with fine particle size and high surface area. Fine particle size allows uniform distribution in an application medium and renders the treatment substantially transparent. Large particle zinc oxide tends to give a white background shade to a textile and therefore affects the appearance of the product. Particle sizes for this application should be preferably below 3 micrometers, most preferably, less than 1 micrometer. Zinc oxide high specific surface area is also preferred for this application. Preferred specific surface area of zinc oxide for this application is 10 $m^2/g$ or more.

The preferred embodiments of these alternatives fabric treatments are discussed in greater detail below.

DESCRIPTION OF THE PREFERRED EMBODIMENTS

Examples of particularly preferred compounds within the scope of the present invention are set forth below. None of the following inventive fabrics exhibited any electrical conductivity.

A) Silver-Particle Yarn and Fabric Treatments

The dispersions used in the durability and log kill study for the resultant articles with silver-particle treatments contained the following concentrations (all % are per weight of solution): 1% $AgNO_3$, 0.5% $NaBH_4$, 5% binder resin, 3% hydroxyethylcellulose thickener, and 90.5% water. The print pattern used was a 12 dpi dot pattern with each dot having ~0.5 mm diameter circular shape.

Three sets of samples were tested at three different numbers of washes. The three sets were: a) untreated 100% polyester multifilament fabric, b) the same type of fabric treated with ust the desired binder resin, and c) the same type of fabric treated with the above-described silver-particle dispersion. Each sample was tested for 0, 15 and 30 washes. To minimize the potential biocidal activity of the detergent, the 15 and 30 wash samples were run through two additional rinse cycles before analysis. In the pertinent Tables which follow, the log kill results were performed with a) an initial *Staphylococcus aureus* concentration of $3.8\times10^6$ CFU/mL and b) a *Klebsiella pneumoniae* inocculum initial concentration of about 18,000,000 CFU/mL.

The following three treatments were performed and shown to be create a highly washfast metal particle finish:

1) Pad Coating

The fabric article (100% polyester fabric) was dipped into a silver particle/polymeric dispersion comprising about 1 part of silver colloid solution and about 5 parts of a binder resin. Particular resins tested were Aerotex(g) M3, Vycar® 460×49, and a PVC/Acrylic resin (all resins available from BFGoodrich). The immersed fabric was then removed and run through a pad roll. The fabric was then heated to 350° C. for 2 minutes. The resulting fabric was then first analyzed for particle count remaining on the fabric surface after treatment by ICP spectroscopy, both initially and after a number of washes utilizing the standard laundering procedure of AATCC Test Method 130-1981. The results are presented in tabular form below:

TABLE 1

Particle Count on Fabrics Pad Coated with Silver Particle Dispersions

| # of Washes | ICP for Silver (ppm) PVC/Acrylic Binder | ICP for Silver (ppm) With Aerotex ® M3 Binder |
|---|---|---|
| 1 | 5210 | 7074 |
| 10 | 3993 | 6250 |
| 20 | 3555 | 6149 |
| 30 | 2841 | 4965 |

Thus, the retention of the metal finish was excellent for both binders (77% after 10 washes, 68% after 20, 55% after 30 for the PVC/Acrylic binder; 88% after 10 washes, 87% after 20, and 70% after 30). It should be noted that these measurements are subject to the variability within the measuring instrument as well; although they are considered relatively and should not deviate in any significant amount from the tabulated results, variations in results may occur. Furthermore, the treated fabrics were also tested for electrical conductivity through the method noted above (AATCC Test Method 76-1978); the noise of the measuring instrument exceeded any signal of the resistance measuring instrument, thus, the resistance is so high for the fabric that no appreciable conductivity was exhibited by all of the tested samples.

2) Yarn Application

In this method, the metal particle dispersion was applied utilizing a kiss-coater, which consists of a roll which constantly rotates in a bath of the metal dispersion. The roll transferred the solution to the top side of the roller, where an end of yam passed against the roller and into an oven where it was cured at 350° C. for 2 minutes then taken up onto a bobbin for further processing. The metal particle coated yam was measured to be electrically non-conductive (by the spaced electrode method noted above) and typically included from about 20 to 30% by weight of the metal-particle dispersion. The silver-coated yam was then knit or woven into a fabric with non-treated yams at a ratio of 1 treated yam to every 15 untreated yams. The treated yams were visible on only one side of the treated fabric and the resultant fabric exhibited excellent sustained antimicrobial performance. Table 3 shows ICP results for silver as a function of washes for a "sock" knit from 70 denier treated yam and 500 denier untreated yam.

TABLE 2

Durability of Silver-Particle Coated Yarns Woven into Fabrics

| # of Home Washes | ICP for Silver (ppm) With Aerotex ® M3 Binder |
|---|---|
| 0 | 3798 |
| 10 | 3709 |
| 20 | 3297 |
| 30 | 3286 |

3) Screen Printing

In a screen printing application, the dispersion described above was thickened and pressed through a printing screen onto one side of a fabric in a finishing step. The preferred thickening agent for this embodiment is Aqualon® Natrosol 99-250 HHR (in a concentration range of 1-10% by weight of solution) with the preferred concentration being 3% (which provides a desired intrinsic viscosity of from about 100,000 to about 400,000, preferably 200,000, centipoise at standard temperature and pressure). The viscosity of the metal particle/polyer dispersion may also be adjusted with the utilization of sufficient amounts of hydroxyethylcellulose; however, mixtures of HEC and the Aqualon® thickeners may prove sufficient to provide a resultant, preferred viscosity of 200,000 cps. Although preferred thickeners for screen printing have been found, one of ordinary skill in this art would appreciate that any number of acceptable thickeners may be utilized, either alone, or in combination, to provide the desired and/or necessity viscosity level in order to perform such a screen printing procedure. The thickened metal-particle containing dispersion was applied to the target fabric by squeezing it through a patterned rotary screen. The "coated" fabric was then cured at 350° F. for at least 2 minutes to produce a coating that washfast through at least 30 washes. Table 4 provides this durability data:

TABLE 3

Durability of Screen Printing on Fabric with Silver-Particle Dispersions

| # of Home Washes | ICP for Silver (ppm) With PVC/Acrylic Binder |
|---|---|
| 0 | 312 |
| 10 | 266 |
| 20 | 135 |
| 30 | 109 |

The treated fabric was then analyzed for its ability to provide antimicrobial effectiveness against *Staphylococcus aureus* and *Klebsiella pneumoniae*. The results were as follows:

TABLE 4

*Staphylococcus aureus* Effectiveness

| # Washes | Control | Binder | Fabric from TABLE 3 |
|---|---|---|---|
| 0 | 0.35 | 0.83 | 5.56 |
| 15 | 1.00 | 1.06 | 4.08 |
| 30 | 0.07 | 1.20 | 5.54 |

TABLE 5

| Klebsiella pneumoniae Effectiveness | | | |
|---|---|---|---|
| # Washes | Control | Binder | Fabric from TABLE 3 |
| 0 | 1.93 | 2.28 | 3.94 |
| 15 | 2.73 | 2.79 | 5.33 |
| 30 | 2.04 | 2.66 | 5.33 |

The durable treatment not only retained its integrity over the target fabric surface, but also continued to provide an effective antimicrobial treatment as well.

B) Silver Ion Exchange, Silver Zeolite, and Zinc Oxide Fabric Treatments As noted above, treatments of specific metal-ion containing compounds have proven to be wash-durable on certain yam and fabric surfaces as well. These include the following, preferably with either the ALPHASAN® silver-based compounds or with zinc oxide. The following preferred embodiments exhibited resistivity measurements well in excess of $1\times10^9$ ohms per square inch of fabric in accordance with AATCC Test Method 76-1978.

1) Exhaustion of Compound Followed with Binder Resin Overcoat a) Acrylic Binder Resin—A dispersion of ALPHASAN® (silver-based ion exchange compound available from Milliken & Company) was first produced through the mixing of about 30% by weight of the silver-based compound, about 23.0% by weight of a mixture of anionic surfactants, Tamol® SN, available from Rohm & Haas, and Synfac® 8337, available from Milliken & Company, and the remainder water. This dispersion was then applied through exhaustion within a dye bath to four fabric samples (all of 100% polyester construction; with 51 picks by 52 ends; 300 denier multifilament yam). Two were dyed at a temperature of about 280° F.; the others at a temperature of about 265° F. The exhaustion level of the active ALPHASAN® compounds on the target fabrics was about 1.0% owf. The fabrics were then coated with an acrylic binder material, Rhoplex® TR3082, in an amount of about 2.5% owf. The coated fabrics were then heat-set at 380° F. The log kill rate for unwashed fabrics for *S. aureus* was measured to be 4.9; for *K. pneumoniae,* 2.54. The results after multiple washings are tabulated below:

TABLE 6

| Log Kill Rates After Multiple Washings With Acrylic Overcoat | | |
|---|---|---|
| Number of Washes | Log Kill Rate for *S. aureus* | Log Kill Rate for *K. pneumoniae* |
| 1 | 4.59 | 2.28 |
| 5 | 4.15 | 2.20 |
| 10 | 3.13 | 1.97 |

It is important to note, and as is well appreciated and understood by one of ordinary in the art, that variations in log kill rate measurements are prevalent, though, reliable, due to inherent difficulties in both biological testing and in the ability to establish completely controlled bacterium counts on such surfaces. These results thus show very favorable antimicrobial performance and thus excellent wash durability on the fabric surface.

b) Permanent Press Binder Resin—The same type of ALPHASAN® dispersion and exhaustion procedure was followed as above. The overcoat, however, was Permafresh®, available from Sequa. Again, about 2.5% owf of this overcoat resin was applied over the ALPHASAN®-treated fabrics. Also added within the dye bath was a butyl benzoate carrier in an amount of about 2.5% owf. The log kill results for this sample were as follows:

TABLE 7

| Log Kill Rates After Multiple Washings With Permanent Press Overcoat | | |
|---|---|---|
| Number of Washes | Log Kill Rate for *S. aureus* | Log Kill Rate for *K. pneumoniae* |
| 0 | 3.21 | 5.32 |
| 1 | 4.11 | 3.89 |
| 5 | 2.98 | 3.03 |
| 10 | 3.94 | 4.23 |

Excellent durability results were thus obtained with such a system.

c) PD-92 Binder Resin—The same type of ALPHASAN® dispersion and exhaustion procedure was followed as above. The overcoat, however, was PD-92 available from Milliken & Company. Again, about 2.5% owf of this overcoat resin was applied over the ALPHASAN®-treated fabrics. Also added within the dye bath was a butyl benzoate carrier in an amount of about 2.5% owf. The log kill results for this sample were as follows:

TABLE 8

| Log Kill Rates After Multiple Washings With PD-92 Overcoat | | |
|---|---|---|
| Number of Washes | Log Kill Rate for *S. aureus* | Log Kill Rate for *K. pneumoniae* |
| 0 | 3.30 | 3.36 |
| 1 | 3.15 | 2.72 |
| 5 | 3.18 | 2.26 |
| 10 | 3.03 | 1.78 |

Excellent durability results were thus obtained with such a system as well.

d) Effect of Increased amount of ALPHASAN® on Wash Durability—The same fabric treatments (with Permafresh® binder resin) as above were performed with the amount of ALPHASAN® increased to a 4% owf active addition to the target fabric surface (about 13.3% owf of the dispersion). The same padding on of the permanent press binder was followed as above. The log kill results for *K. pneumoniae* are as follows:

TABLE 9

| Log Kill Rates With High Add-On of Silver-Based Compound | |
|---|---|
| Number of Washes | Log Kill Rate for *K. pneumoniae* |
| 0 | 5.6 |
| 5 | 5.7 |
| 10 | 4.4 |

Again, excellent durability was obtained.

e) Effect of Increased amount of Permanent Press Binder Resin on Wash Durability—The same fabric treatments (with Permafresh® binder resin) as above were performed with the padded on amount of binder resin increased to a 7.5% owf addition to the target fabric surface. The log kill results for *K. pneumoniae* are as follows:

TABLE 10

Log Kill Rates With High Add-On of Permanent Press Binder Resin

| Number of Washes | Log Kill Rate for *K. pneumoniae* |
|---|---|
| 0 | 5.7 |
| 5 | 4.0 |
| 10 | 3.9 |

Again, excellent wash durability results were obtained.

2) Exhaustion of Compound with a Binder Resin

A dispersion of ALPHASAN® (silver-based ion exchange compound available from Milliken & Company) was first produced through the mixing of about 30% by weight of the silver-based compound, about 23.0% by weight of an anionic surfactant mixture of Tamol® and Synfact 8337 surfactant, and the remainder water. This dispersion was then applied through exhaustion within a dye bath which included an acrylic binder (Rhoplex® TR3082) which was present within the dye bath in a concentration of about 2.5% owf. A 100% polyester fabric (same as above) was then placed within the dye bath which was then heated to a temperature of about 280° F. The exhaustion level of the active ALPHASAN® compounds on the target fabrics was about 1.0% owf. The fabrics were then heat-set at 380° F. The log kill rate for unwashed fabrics for *S. aureus* was measured to be 2.35; for *K. pneumoniae,* 5.38. The results after multiple washings are tabulated below:

TABLE 11

Log Kill Rates After Multiple Washings With Acrylic Resin

| Number of Washes | Log Kill Rate for *S. aureus* | Log Kill Rate for *K. pneumoniae* |
|---|---|---|
| 1 | 1.50 | 2.37 |
| 5 | 1.17 | 2.37 |
| 10 | 1.36 | 2.98 |

These results show very favorable antimicrobial performance and thus excellent wash durability on the fabric surface, though less favorable than for the resin overcoated fabrics.

3) Exhaustion of Other Silver-Based Compounds

The same general exhaustion methods were followed as above with the same padding on (denoted as P in the table below) and dye bath application (D in the following table) of a permanent press binder as above as well. The different silver-based compounds applied were AmpZ200 (a TiO2/silver metal product available from DuPont), and ZEOMIC® AJ80H. The add-on weights of these were the same 1.0% owf treatment as for the ALPHASAN® noted above. The durability results for these compounds were as follows for *K. pneumoniae* log kill rates:

TABLE 12

Log Kill Rates With Other Silver-Based Compounds

| Compound | Number of Washes | Log Kill Rate for *K. pneumoniae* |
|---|---|---|
| AmpZ200 (P) | 0 | 2.76 |
| AmpZ200 (P) | 10 | 1.82 |
| AmpZ200 (D) | 0 | 2.06 |
| AmpZ200 (D) | 10 | 1.36 |
| ZEOMIC ® AJ80H (P) | 0 | 5.31 |
| ZEOMIC ® AJ80H (P) | 10 | 1.64 |
| ZEOMIC ® AJ80H (D) | 0 | 4.31 |
| ZEOMIC ® AJ80H (D) | 10 | 1.92 |

These are excellent durability results, although not as good as for the ALPHASAN® treatments.

4) Package Dyeing Method

Again, as with al of the other inventive fabrics and yams, the measured resistivity of the following yams and fabrics exceeded $1\times10^9$ ohms per square inch.

EXAMPLE 1

Several spools of 150 denier polyester multifilament yarn were placed within a sealed dye bath. The dye bath liquor contained 1.0% owf of active ALPHASAN®, 0.5% by weight of nonionic leveler 528 (butyl benzoate, available from Milliken & Company), and the balance water. After sealing of the chamber, the pump was activated at a pressure of 60 psi at a temperature of about 280° F. The pump remained activated for about 60 minutes. The resultant spools of yam were then utilized in a knitting operation to produce a sock. Three different discrete areas of the sock were tested for log kill rates for *K. pneumoniae* after different numbers of launderings. The colorations of the sock remained virtually the same after such repeated launderings. The log kill results are tabulated below:

TABLE 13

Log Kill Rates On The Knit Fabrics (Binder-Free)

| Number of Washes | Log Kill Rate for *K. pneumoniae* |
|---|---|
| 0 | 4.43 |
| 5 | 4.13 |

The knit fabric thus retained a substantial amount of its ALPHASAN® finish applied during the package dyeing process for an extremely long duration.

EXAMPLE 2

Several spools of 150 denier multifilament polyester yam were placed within a sealed dye bath. The dye bath liquor contained 1.0% owf of active ALPHASAN®, 0.5% owf nonionic leveler 528, 2.0% owf of Rhoplex® TR3082 (an acrylic-based slightly anionic binding agent), and the balance water. After sealing of the chamber, the pump was activated at a pressure of 60 psi at a temperature of about 280° F. The pump remained activated for about 60 minutes. The resultant spools of yam were then utilized in a knitting operation to produce a sock. Three different discrete areas of the sock were tested for log kill rates for *K. pneumoniae* after different numbers of launderings. The colorations of the sock remained virtually the same after such repeated launderings. The log kill results are tabulated below:

TABLE 14

Log Kill Rates On The Knit Fabrics (With Acrylic Binder)

| Number of Washes | Log Kill Rate for *K. pneumoniae* |
|---|---|
| 0 | 4.43 |
| 5 | 4.20 |
| 10 | 4.03 |

The knit fabric thus retained a substantial amount of its ALPHASAN® finish applied during the package dyeing process for an extremely long duration.

EXAMPLE 3

Several spools of 150 denier multifilament polyester yarn were placed within a sealed dye bath. The dye bath liquor contained 1.0% owf of active ALPHASAN®, 0.5% owf of nonionic leveler 528, and the balance water. After sealing of the chamber, the pump was activated at a pressure of 60 psi at a temperature of about 280° F. The pump remained activated for about 60 minutes. The resultant spools of yarn were then utilized in a knitting operation to produce a sock. A permanent press binding agent (2.0% owf of Permafresh®, available from Sequa) was then padded on the entire sock. After drying, three different discrete areas of the sock were tested for log kill rates for *K. pneumoniae* after different numbers of launderings. The colorations of the sock remained virtually the same after such repeated launderings. The log kill results are tabulated below:

TABLE 15

Log Kill Rates On The Knit Fabrics (With Permanent Press Binder)

| Number of Washes | Log Kill Rate for *K. pneumoniae* |
|---|---|
| 0 | 4.43 |
| 5 | 4.42 |
| 10 | 3.85 |

The knit fabric thus retained a substantial amount of its ALPHASAN® finish applied during the package dyeing process for an extremely long duration.

Metal Oxide Odor Reduction Fabric Treatments

A dispersion having the following components was mixed thoroughly:

COMPOSITION

| Component | Amount (in grams) |
|---|---|
| Zinc oxide powder (Aldrich, <1 micron) | 2.0 grams |
| Rhoplex ® E-32NP (acrylic resin binder) | 8.0 grams |
| Millitex ® PD-92 (wetting agent) | 2.0 grams |
| Ultratex ® MES (fabric softener) | 0.5 grams |
| water | 90 grams |

One swatch of dyed knit polyester fabric was impregnated with the mixed solution and dried at 350° F. for 3 min to obtain a treated fabric. The treated fabric exhibited no noticeable color or flexibility change. Several drops of a dilute aqueous isovaleric acid solution (1 drop of acid in 50 grams of water), to simulate unpleasant foot odor, was then applied to the unwashed fabric. The solution quickly wicked into the fabric and the unpleasant odor quickly disappeared. The treated fabric was then laundered in accordance with the AATCC Test Method 130-1981 for 10 cycles; the same wicking and odor removal was exhibited by the zinc oxide treated fabric. Thus, the zinc oxide treatment remained intact on the fabric surface. Furthermore, the sample was tested for electrical conductivity by measuring resistance over the entire fabric. The fabric sample exhibited $10^{13}$ ohms/square inch of fabric; thus, effectively no conductivity existed.

The sample was then washed in accordance with AATCC Test Method 130-1981 and then analyzed for odor reduction and antimicrobial activity in accordance with 24 hour inoculation exposure of *Klebsiella pneumoniae* under AATCC Test Method 100-1983. The results were as follows:

TABLE 16

| # of Washes | Log Kill Reduction | Odor Neutralization? |
|---|---|---|
| 1 | 3.1 | Yes |
| 10 | 3.6 | Yes |
| 25 | ~3.0 | Yes |

Furthermore, X-ray fluorescence was performed on the above sample to indicate the amount of zinc retained on the fabric surface as well through the peak size in relation to the signal emitted by zinc on the substrate surface. The results were as follows:

TABLE 17

| Number of washes | Zinc X-ray counts |
|---|---|
| 0 | 162,644 |
| 2 | 113,133 |
| 10 | 87,471 |
| 20 | 49,801 |

Thus, excellent wash durability was exhibited even after twenty washes since about 30% was retained from the initial zinc count.

Lightfastness of Certain Samples

The samples tested in TABLE 6, above, as well as other fabrics and comparative samples were analyzed for the lightfastness of the color exhibited by the treated fabrics after topical application of the desired metal-based finish. Such analysis involved testing in accordance with The Engineering Society for Advancing Mobility Land Sea Air and Space Textile Test method SAE J-1885, "(R) Accelerated Exposure of Automotive Interior Trim Components Using a Controlled Iradiance Water Cooled Xenon-Arc Apparatus." Colorlightfastness is generally calculated by the following equation:

$$\Delta E^* = ((L_{initial}^* - L_{exposed}^*)^2 + (a_{initial}^* - a_{exposed}^*)^2 + (b_{initial}^* - b_{exposed})^2)^{1/2}$$

wherein ΔE* represents the difference in color between the fabric upon initial latex coating and the fabric after the above-noted degree of ultra violet exposure. L*, a*, and b* are the color coordinates; wherein L* is a measure of the lightness and darkness of the colored fabric; a* is a measure of the redness or greenness of the colored fabric; and b* is a measure of the yellowness or blueness of the colored fabric. A low ΔE* shows excellent lightfastness for the tested fabric; a ΔE* greater than about 5.0 is unacceptable and shows a yellowing tendency for the treated fabric. As noted above, the ALPHASAN®-treated polyester sample from TABLE 6 was subjected to a Xenon Arc Lamp Test at 225 kJ/$m^2$ for both 20 and 40 hours to analyze the yellowing characteristics of the treated fabric. At 20 hours, the fabric exhibited a ΔE* of about 1.95; at 40 hours, a ΔE* of about 3.38. Thus, the treated fabric exhibited excellent lightfastness properties.

Further samples of 65%/35% polyester/cotton blend shirts were also tested for such lightfastness results after receiving ALPHASAN® treatments from dryer donor sheets comprising 0, 9%, and 20% (made in accordance with the method discussed above) of the silver-based ion exchange compound. The results were tabulated as follows:

TABLE 18

| Amount of ALPHASAN ® | ΔE* at 20 hours | ΔE* at 20 hours |
|---|---|---|
| 0 | 0.48 | 0.72 |
| 9 | 1.03 | 1.23 |
| 20 | 1.34 | 1.82 |

Clearly and surprisingly, the silver treated fabrics exhibited acceptable lightfastness characteristics.

There are, of course, many alternative embodiments and modifications of the present invention which are intended to be included within the spirit and scope of the following claims.

What we claim is:

1. A treated substrate comprising a finish comprising metal compounds selected from the group consisting of silver particle-containing compounds, silver ion-containing compounds, silver ion-generating compounds, and any combinations thereof, and a substrate selected from the group consisting of a yarn, a fabric comprised of individual fibers, and a film;

wherein said finish is adhered to at least one portion of the surface of said substrate;

wherein said at least one portion of said treated substrate retains at least about 50% of said adhered to finish after 10 washes as performed in accordance with the wash procedure of AATCC Test Method 130-1981;

wherein said finish contains a binder agent and 0.1 to 40 weight percent of the metal compound, or wherein the at least one portion of said treated substrate is covered with a binder formulation;

wherein said treated substrate is electrically non-conductive; and wherein said finish exhibits antimicrobial properties.

2. The treated substrate of claim 1, wherein said substrate is an individual yarn.

3. The treated substrate of claim 1, wherein said substrate is a textile fabric.

4. The treated substrate of claim 1, wherein said substrate is a film.

5. A treated substrate of claim 1, exhibiting a log kill rate for *Staphylococcus aureus* of at least 1.5 and a log kill rate for *Klebssiella pneumoniae* of at least 1.5, both as tested in accordance with AATCC Test Method 100-1993 for 24 hour exposure, after at least 10 washes, said washes performed in accordance with the wash procedure as part of AATCC Test Method 130-1981.

6. The treated substrate of claim 1, wherein the metal compound is a silver ion-containing compound.

7. The treated substrate of claim 1, wherein the metal compound is present in an amount of between 0.01 to 1.0 ounces per square yard.

8. The treated substrate of claim 1, wherein the substrate is a fabric comprised of cotton fibers, wool fibers, ramie fibers, hemp fibers, linen fibers, polyolefin fibers, polyester fibers, polyamide fibers, polyaramid fibers, acetate fibers, rayon fibers, acrylic fibers, or blends thereof.

9. The treated substrate of claim 8, wherein the substrate is a fabric comprised of polyester fiber.

10. The treated substrate of claim 1, wherein the binder is selected from the group consisting of cross-linked imidazolidinones, acrylic binders, melamine resins, polyvinyl chloride-containing polymers, ethoxylated polyesters, or blends thereof.

11. The treated substrate of claim 1, wherein the binder is anionic or nonionic, and wherein the binder, after processing and application to the substrate:

(a) is not readily soluble in water, (b) is not susceptible to attack by standard laundering additives selected from the group consisting of detergents, solvents, bleaches, and mixtures thereof, and (c) is not susceptible to degradation due to exposure to high temperatures associated with standard laundry drying temperatures.

12. The treated substrate of claim 6, wherein the silver ion-containing compound is silver zirconium phosphate.

* * * * *